United States Patent
Guthrie et al.

(10) Patent No.: US 9,395,319 B2
(45) Date of Patent: Jul. 19, 2016

(54) ANALYTICAL TEST METER

(71) Applicant: LifeScan Scotland Limited, Inverness, Iverness-shire (GB)

(72) Inventors: Brian Guthrie, Inverness (GB); Tim Lloyd, Inverness (GB); Yeswanth Gadde, Inverness (GB); Alexander Strachan, Inverness (GB); David Elder, Inverness (GB); Rossano Massari, Milan (IT); Christian Forlani, Milan (IT)

(73) Assignee: LifeScan Scotland Limited, Inverness (GB)

( * ) Notice: Subject to any disclaimer, the term of this patent is extended or adjusted under 35 U.S.C. 154(b) by 548 days.

(21) Appl. No.: 13/875,487

(22) Filed: May 2, 2013

(65) Prior Publication Data

US 2014/0326614 A1    Nov. 6, 2014

(51) Int. Cl.
*G01N 27/30* (2006.01)
*G01N 27/327* (2006.01)

(52) U.S. Cl.
CPC .......... *G01N 27/307* (2013.01); *G01N 27/3273* (2013.01); *G01N 27/3274* (2013.01)

(58) Field of Classification Search
None
See application file for complete search history.

(56) References Cited

U.S. PATENT DOCUMENTS

| | | | |
|---|---|---|---|
| 3,906,890 A | 9/1975 | Amos et al. | |
| 6,540,891 B1 | 4/2003 | Stewart et al. | |
| 7,090,764 B2 | 8/2006 | Iyengar et al. | |
| 7,569,126 B2 | 8/2009 | Celentano et al. | |
| RE41,946 E | 11/2010 | Anderson et al. | |
| 8,343,331 B2 | 1/2013 | Choi | |
| 8,404,100 B2 | 3/2013 | Wu | |
| 2003/0109798 A1* | 6/2003 | Kermani | G01N 27/3273 600/547 |
| 2011/0089957 A1 | 4/2011 | Sheppard, Jr. | |
| 2011/0303556 A1 | 12/2011 | Chen et al. | |
| 2013/0084589 A1* | 4/2013 | Kraft | G01N 27/3273 435/14 |

FOREIGN PATENT DOCUMENTS

| | | |
|---|---|---|
| EP | 1394545 A1 | 3/2004 |
| EP | 2535705 A1 | 12/2012 |
| WO | WO2013030375 A1 | 3/2013 |

OTHER PUBLICATIONS

International Search Report and Written Opinion issued in related International Application No. PCT/EP2014/059013, mailed Jun. 17, 2014, 9 pages.

* cited by examiner

*Primary Examiner* — Luan Van
*Assistant Examiner* — Steven Rosenwald

(57) ABSTRACT

A portable analytical test meter is designed for use with an associated analytical test strip. A test-strip-receiving module receives the analytical test strip and is electrically connected to a dummy load calibration circuit block. That block is configured to provide a dummy magnitude correction and a dummy phase correction; and a memory block is configured to store the dummy magnitude correction and the dummy phase correction. A method for calibrating a portable analytical test meter for use with an analytical test strip includes determining a dummy magnitude correction and a dummy phase correction of the portable analytical test meter using a dummy load calibration circuit block of the portable analytical test meter. The dummy magnitude correction and the dummy phase correction are stored in a memory block of the portable analytical test meter. Using the stored dummy magnitude correction and stored dummy phase correction, an analyte is determined.

17 Claims, 8 Drawing Sheets

ANALYTICAL TEST METER

TECHNICAL FIELD

The present application relates generally to the field of medical devices, and particularly to analytical test meters, and related methods, for measuring an analyte of a patient sample, such as blood glucose or hematocrit.

BACKGROUND

The determination (e.g., detection or concentration measurement) of an analyte in a fluid sample is of particular interest in the medical field. For example, it can be desirable to determine glucose, ketone bodies, cholesterol, lipoproteins, triglycerides, acetaminophen or glycosylated hemoglobin (HbA1c) concentrations in a sample of a bodily fluid such as urine, blood, plasma or interstitial fluid. Such determinations can be achieved using an analytical test strip and test meter combination. For example, a diabetic patient conventionally tests his or her blood glucose using an analytical test meter and a disposable test strip. The user inserts the disposable test strip into the analytical test meter, then applies a drop of his or her blood to a sample-receiving chamber on the test strip. The analytical test meter applies test electrical signals to the blood in the sample-receiving chamber via electrodes and conductors on the test strip, and monitors resulting electrical signals. A processor in the analytical test meter can then determine the user's blood glucose (e.g., in mg glucose per dL of blood, or mmol glucose per L of blood) using the resulting electrical signals.

However, various factors can confound or interfere with such determinations. For example, U.S. Pat. No. 7,390,667 to Burke et al. describes that reagents in the sample-receiving chamber are used to provide charge carriers that are not otherwise present in blood. Consequently, the electrochemical response of the blood in the presence of a given signal is intended to be primarily dependent upon the concentration of blood glucose. Secondarily, however, the electrochemical response of the blood to a given signal is dependent upon other factors, including temperature and hematocrit (HCT), the percentage by volume of red blood cells in the blood.

U.S. Pat. No. 8,343,331 to Choi describes a method of correcting erroneous measurement results in a biosensor. A first voltage is applied to a blood sample on a test strip and a hematocrit value of the blood sample is calculated using a measured electric current value. A second voltage is then applied, and a glucose level is calculated using a second measured electric current value. The glucose level is corrected by using the calculated hematocrit value. However, this requires an accurate measurement of hematocrit to provide results of a desired accuracy.

BRIEF DESCRIPTION OF THE DRAWINGS

Various features and advantages of the present invention will become more apparent when taken in conjunction with the following description and drawings wherein identical reference numerals have been used, where possible, to designate identical features that are common to the figures, and wherein.

The attached drawings are for purposes of illustration and are not necessarily to scale.

DETAILED DESCRIPTION

Even in analytical test meters that measure hematocrit (HCT) to more accurately determine blood glucose, the hematocrit level measurement can be affected by parasitic electrical properties, e.g., parasitic capacitances, on printed circuit boards in the analytical test meter or in the test strip. Described herein are various ways of detecting and correcting for some such parasitic properties in various test meters for various analytes in various fluids.

Figure 1:
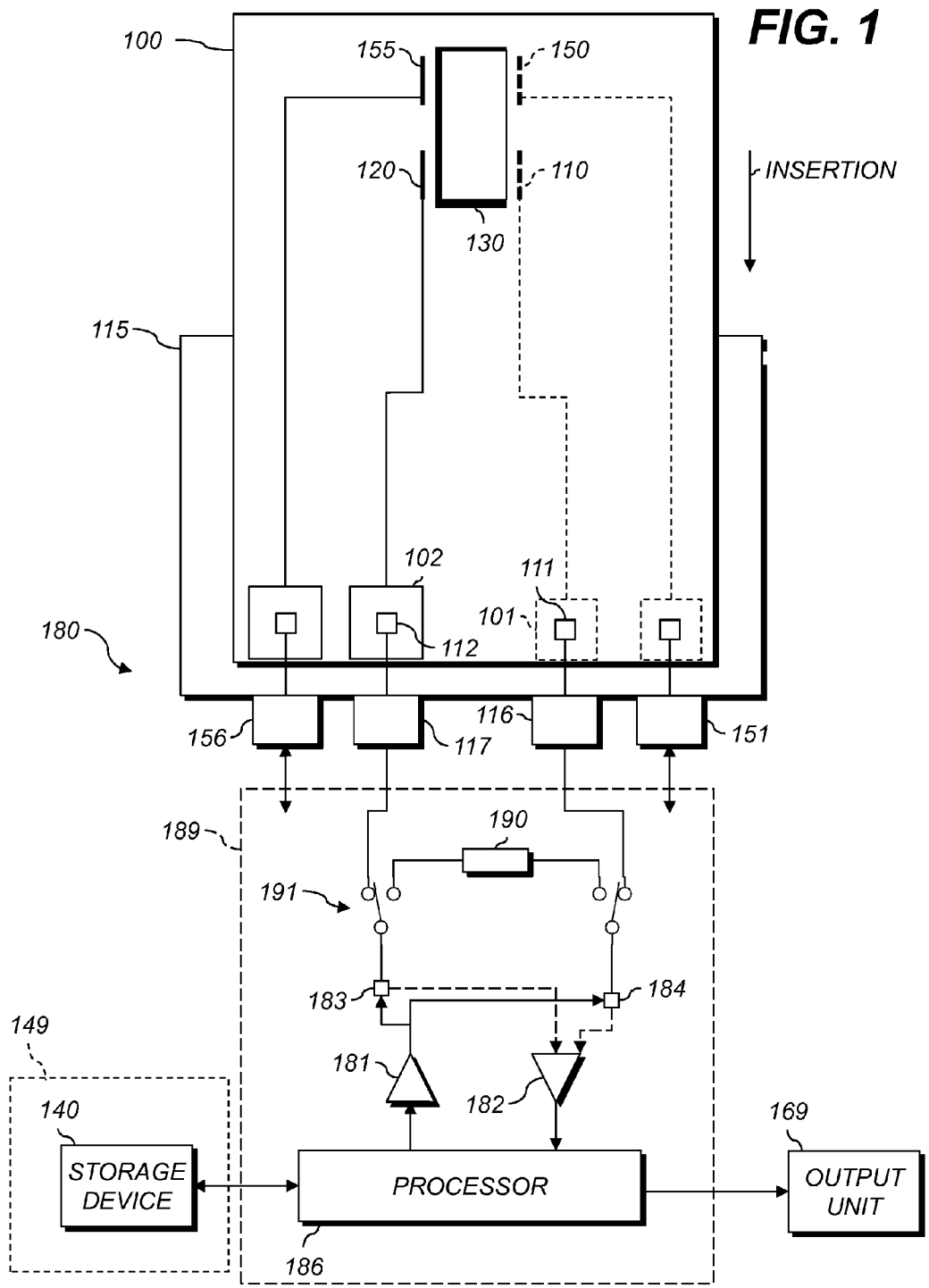
FIG. 1 is a schematic representation of components of an exemplary analytical test system including a analytical test meter and test strip.

FIG. 1 is a schematic representation of components of an analytical test system according to various aspects. A "test set" or "test pairing" is such a system including a test strip 100 and an analytical test meter 180, e.g., a portable analytical test meter. The analytical test meter 180 can be, e.g., a hand-held test meter, and can include a housing. The analytical test meter 180 can also be clipped onto, or otherwise fastened to, a belt or strap, e.g., for placement place around the waist or over the shoulder of a user.

The analytical test system is adapted to determine an analyte in a fluid sample, e.g., a bodily-fluid sample. The analytical test meter 180 includes a test-strip-receiving module 115, also referred to herein as a "strip port connector" or SPC. The test-strip-receiving module 115 can include electrical or mechanical structures adapted to receive or retain a test strip 100. According to the exemplary version, the test-strip-receiving module 115 has at least first and second electrical connector pins 111, 112. For purposes described herein, the term "pin" does not limit form factor; that is, pins 111, 112 can be rigid pins, spring contacts, pogo pins, pressure contacts, solder bumps, or other electrically-conductive contacting devices.

The processor 186 controls operation of the analytical test system. As described herein, the processor 186 can include a microcontroller, microprocessor, field-programmable gate array (FPGA), programmable logic array or device (PLA or PLD), programmable array logic (PAL) device, digital signal processor (DSP), or other logic or processing component adapted to perform functions described herein, or more than one of any of those, in any combination.

The exemplary test strip 100 has first and second electrodes 110, 120 operatively arranged with respect to a sample-receiving chamber 130, also referred to herein as an analyte chamber. The first electrical contact pad 101 is electrically connected to the first electrode 110. The first electrical contact pad 101 is configured to communicate an electrical response of the first electrode 110 to the analytical test meter 180 in electrical communication with the first contact pad 101, e.g., by making contact when the test strip 100 is properly inserted within the confines of the test-strip-receiving module 115. The test strip 100 can include a variety of electrical contact configurations for electrically connecting to the analytical test meter 180. For example, U.S. Pat. No. 6,379, 513 discloses electrochemical cell connections, and is hereby incorporated by reference in its entirety.

The second electrical contact pad 102 is electrically connected to the second electrode 120 and is configured to communicate an electrical response of the second electrode 120 to the analytical test meter 180 when the analytical test meter 180 is in electrical communication with the second electrical contact pad 102. The test-strip-receiving module 115 is arranged such that the first and second electrical connector pins 111, 112 make electrical connection with the first and second electrical contact pads 101, 102, respectively, when the test strip 100 is inserted into the test-strip receiving module 115. The processor 186 or related components are electrically connected to conductors 116, 117, which are electrically connected to pins 111, 112 respectively.

The processor 186 can detect the presence of the inserted test strip 100 by sensing electrical properties between first and second electrical connector pins 111, 112. For example, the processor 186 can detect a change in capacitance between the connector pins 111, 112 when the test strip 100 is inserted. The test strip 100 can include a third electrical contact pad (not shown) electrically connected to either the first electrical contact pad 101 or the second electrical contact pad 102. The test-strip-receiving module 115 can include a third electrical pin, and the processor 186 can detect continuity between two of the pins of the test-strip-receiving module 115 as indicating insertion of a test strip 100. The analytical test meter 180 can also include a mechanical, optical, or electromechanical element, e.g., a reed switch or optointerruptor, to determine when the test strip 100 has been properly inserted. The processor 186 can wait for a test strip, prompt for a strip, or take other actions until the test strip 100 is detected, e.g., perform calibration steps. The processor 186 can also enter a low-power mode, e.g., a sleep mode, until the presence of a test strip 100 is first detected. In an example, the user presses a button after inserting the test strip. The processor 186 detects insertion of the test strip when the button is pressed. This, and other examples in this paragraph, can be used for any strip detection described herein.

When the test strip 100 is detected, the processor 186 applies a selected electrical signal across the first and second electrical pins 111, 112 using an excitation source 181. The excitation source 181 can be a voltage source, current source, arbitrary waveform source, or other device adapted to produce electrical signals. The processor 186 then measures a result electrical signal on pins 111, 112 using a demodulator 182. The demodulator 182 can include an analog to digital converter (ADC), sample-and-hold unit, mixer unit, or other device that is suitably adapted to measure electrical signals. In an example, a voltage is applied between the connector pins 111 and 112 and the resulting current through those pins is measured.

The excitation source 181 and the demodulator 182 can be connected to conductors 116, 117 through respective couplers 183, 184 that can include pass transistors, RF couplers or gates, or other devices adapted to permit excitation source 181 to apply signals to electrical conductors 116, 117 and to permit the demodulator 182 to, simultaneously or not, measure electrical properties of conductors 116, 117 or signals carried thereon. According to this exemplary embodiment, the couplers 183, 184 can include electrical shorts, so the output of excitation source 181 is connected directly to the input of the demodulator 182, and the processor 186 or demodulator 182 can include echo-suppression or echo-cancellation circuitry, logic, or code (not shown) to remove the output of the excitation source 181 from the received signal.

In FIG. 1, the couplers 183, 184 are represented graphically as squares. For clarity, connections to the demodulator 182 are shown dashed.

The processor 186 processes the result electrical signal to detect the fluid sample and, if the fluid sample is present, to determine the analyte, e.g., to determine concentration or identity of the analyte. This determination is discussed below. In various embodiments, the processor 186 communicates an indication of the determined analyte, or other status information (e.g., "no strip present" or "no sample present") using output unit 169. The output unit 169 can present various visible or audible indicators corresponding to the indication of the determined analyte. For example, the output unit 169 can include a light that lights or blinks, a bell, beeper or buzzer that sounds, a horn that blows, an audio- or visual-reproduction system that activates (e.g., a computer screen that displays a pop-up error dialog), or a network interface that transmits information corresponding to the indication to a human-machine interface (HMI), server, terminal, smartphone, pager, or other computing or communications device. Any of these devices can operate to communicate the indication (e.g., the light can be defined by an illumination level that is proportional to a determined concentration of the analyte).

Still referring to FIG. 1, an electrochemical (amperometric) method for measuring an analyte concentration in a fluid sample, e.g., a bodily-fluid sample or an aqueous sample, involves placing the sample into a reaction zone in an electrochemical cell (e.g., sample-receiving chamber 130) that has two electrodes (e.g., electrodes 110, 120) having an impedance that is suitable for the amperometric measurement. The analyte is allowed to react directly with an electrode (e.g., with one of the electrodes 110, 120) or with a redox reagent to form an oxidizable (or reducible) substance in an amount that corresponds to the analyte concentration. The quantity of oxidizable (or reducible) substance is then determined electrochemically. Various aspects accurately determine the point in time at which the sample is detected in the reaction zone. This determination permits an electrochemical waveform (e.g., voltage) to be applied immediately after the sample has been applied and accurately defines an incubation period or reaction time. In turn, the accuracy and precision of the assay are improved.

As will be discussed below, an enzyme can be present in the sample-receiving chamber 130, or not. If present, the enzyme can assist in transducing the analyte in the fluid sample into a current, potential, or other quantity that can be measured electrically. The frequency and amplitude of signals from the excitation unit 181 can be selected according to various factors, e.g., the nature of the fluid sample, the nature of the analyte, or whether or not the electrodes to be used are operatively arranged with respect to an enzyme.

In an exemplary embodiment, more than two electrode pairs are operatively arranged with respect to the sample-receiving chamber 130. In the example shown, electrodes 150 and 155 are arranged to react with the fluid sample in the sample-receiving chamber 130. The electrodes 150, 155 are connected through respective conductors and pins to conductors 151, 156 respectively on the test-strip-receiving module 115. As represented by the arrows extending from the conductors 151, 156 into the dummy load calibration circuit block 189, the electrodes 150, 155 can be electrically connected to the excitation source 181, the demodulator 182, the switching unit 191, or the processor 186. In various aspects, the electrodes 150, 155 do not have an enzyme coated on them or otherwise operatively arranged with respect to them. In an example, the electrodes 150, 155 are used for Hct measurement and are connected to the excitation source 181 and the demodulator 182 through the switching unit 191.

In various versions, first, a small, constant current source is applied across the electrodes 110, 120 of an electrochemical diagnostic strip and a potential difference between the electrodes 110, 120 is monitored. Before the sample is applied to the sample-receiving chamber 130 of the test strip 100, there is a dry gap between the electrodes 110, 120. Therefore, negligible current flows and the voltage difference between the electrodes 110, 120 increases. When a sample is applied to the test strip 100 and fills the gap (sample-receiving chamber 130), the measured voltage decreases rapidly, causing the test time to be initiated. The processor 186 recognizes the decrease in voltage as indicative of a sample and automatically stops applying a constant-current electrical signal to the selected pins (e.g., pins 111 and 112). The processor 186 then applies a constant-voltage electrical signal to the selected pins. While the constant voltage is applied, current or charge can be measured as a function of time in order to permit the analyte concentration to be calculated.

In other embodiments, once a test strip has been inserted and that insertion has been detected, a bias (e.g., 400 mV) is applied across the electrodes 110, 120. The current between the electrodes 110, 120 is measured. When the current exceeds a selected threshold (e.g., 150 nA), a fluid sample (e.g., a blood sample) is detected. The time at which the sample is detected is used as a reference time (T=0) for calibration and measurements relating to the inserted test strip.

The current measured a predetermined time after the constant voltage is applied is a measure of the analyte concentration, once the system has been calibrated using samples having known analyte concentrations. The duration of the predetermined time is not critical. For example, the duration of the predetermined time can be at least about 3 seconds when the fluid is blood and the analyte to be detected is glucose. This duration generally provides sufficient time to dissolve reagents and reduce an amount of mediator that is readily measurable. All things being equal, and when a sample includes a high level of hematocrit, longer times are needed. Therefore, the duration can be <10 seconds. The same predetermined time can be used for multiple successive measurements of respective samples. Further examples are given in U.S. Pat. No. 6,193,873, incorporated herein by reference.

In various aspects, the test strip 100 can include opposed first and second sides (not shown). The second side can include an electrically-insulating layer disposed over the second electrode 120. Each of the second electrically-insulating layer and second electrode 120 can include corresponding first and second cutout portions that expose corresponding areas of the first electrode 110 to define two electrically-connected electrical contact pads: pad 102 and a pad useful for detecting the test strip 100 by determining connectivity. In various embodiments, the first and second cutout portions are arranged on opposing lateral sides of the test strip 100. Other embodiments of a test strip 100 are described below with reference to FIG. 5.

Electrodes 110, 120 can be stacked above and below the sample-receiving chamber 130. In various aspects, the second electrode 120 is electrically insulated from the first electrode 110 in a sandwiched format. In one version, the first electrode 110 includes gold (Au) and electrode 120 includes palladium (Pd). The electrodes, e.g., electrodes 110, 120, can be thin films. In various versions, the electrodes include conductive material formed from materials such as gold, palladium, carbon, silver, platinum, tin oxide, iridium, indium, and combinations thereof (e.g., indium-doped tin oxide or "ITO"). Electrodes can be formed by disposing a conductive material onto electrically-insulating layers by a sputtering, electroless plating, or screen printing process. In an example, sputtered gold electrode 110 is disposed over one side of the test strip 100, and sputtered palladium electrode 120 is disposed over the remaining side. Suitable materials that can be employed as electrically-insulating layers to separate the electrodes 110, 120 include, for example, plastics (e.g. PET, PETG, polyimide, polycarbonate, polystyrene), silicon, ceramic, glass, and combinations thereof, e.g., 7-mil-thick polyester. Details of various exemplary test strips and measurement methods are provided in US Patent Application Publication No. 2007/0074977, incorporated herein by reference.

In various aspects, the sample-receiving chamber 130 is adapted for analyzing small volume samples. For example, the sample-receiving chamber 130 can have a volume ranging from about 0.1 microliters to about 5 microliters, or 0.2 to about 3 microliters, or about 0.3 microliters to about 1 microliter. To accommodate a small sample volume, the electrodes 110 and 120 can be closely spaced. For example, where a spacer (not shown) defines the distance between the second electrode 120 and the first electrode 110, the height of the spacer can be in the range of about 1 micron to about 500 microns, or between about 10 microns and about 400 microns, or between about 40 microns and about 200 microns. More details relating to exemplary test strips are given in U.S. Pat. No. 8,163,162, incorporated herein by reference.

A reagent layer (not shown) can be disposed within the sample-receiving chamber 130 using a process such as slot coating, coating by dispensing liquid from the end of a tube, ink jetting, and screen printing. Such processes are described, for example, in the following U.S. Pat. Nos. 6,749,887; 6,689,411; 6,676,995; and 6,830,934, each of which is incorporated by reference herein. In various embodiments, the reagent layer is deposited onto an electrode (e.g., electrode 120) and includes at least a mediator and an enzyme. A mediator can be in either of two redox states which may be referred to as an oxidizable substance or a reducible substance. Examples of suitable mediators include ferricyanide, ferrocene, ferrocene derivatives, osmium bipyridyl complexes, and quinone derivatives. Examples of suitable enzymes include glucose oxidase, glucose dehydrogenase (GDH) based on a pyrroloquinoline quinone co-factor, and GDH based on a nicotinamide adenine dinucleotide co-factor. One exemplary reagent formulation for the reagent layer is described in U.S. application Ser. No. 10/242,951, entitled, Method for Manufacturing a Sterilized and Calibrated Biosensor-Based Medical Device, published as U.S. Patent Application Publication No. 2004/0120848, which is hereby incorporated by reference in its entirety.

In an example, the electrode 120 is a working electrode formed by sputtering a Pd coating on a polyester base. A dry reagent layer is used and includes buffer, mediator, and enzyme, as described herein. A spacer between the electrodes 110 and 120 has a cutout area that defines an electrochemical cell (sample-receiving chamber 130). The spacer can be less than about 200 μm thick. The electrode 110 is a reference electrode formed by sputtering an Au coating on a polyester base. In this example, a glucose oxidase/ferricyanide system is used to determine glucose concentrations via the following reactions:

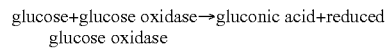
Reaction 1:

glucose+glucose oxidase→gluconic acid+reduced glucose oxidase

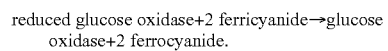
Reaction 2:

reduced glucose oxidase+2 ferricyanide→glucose oxidase+2 ferrocyanide.

Ferricyanide ($[Fe(CN)_6]^{3-}$) is the mediator, which returns the reduced glucose oxidase to its catalytic state. Glucose oxidase, an enzyme catalyst, will continue to oxidize glucose so long as excess mediator is present. Ferrocyanide ($[Fe(CN)_6]^{4-}$) is the product of the total reaction. Ideally, there is no ferrocyanide initially, although in practice there is often a small quantity. After the reaction is complete, the concentration of ferrocyanide (measured electrochemically) indicates the initial concentration of glucose. The total reaction is the sum of reactions 1 and 2:

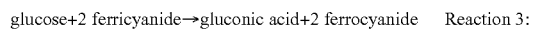

glucose+2 ferricyanide→gluconic acid+2 ferrocyanide    Reaction 3:

"Glucose" refers specifically to β-D-glucose. Details of this system are described in PCT Application No. WO 97/18465 and U.S. Pat. No. 6,444,115, each of which is incorporated herein by reference.

In an example, the analytical test meter 180 measures glucose level and other properties of a drop of blood on a test strip 100. One of those other properties can be hematocrit. HCT and glucose measurements are confounded, so measuring HCT permits determining glucose more accurately. The test strip 100 includes the sample-receiving chamber 130 that holds the drop of blood, pads 101, 102 to connect to connector pins 111, 112 in the analytical test meter 180, and the electrodes 110, 120 carrying signals between the pads 101, 102 and the sample-receiving chamber 130. In some aspects, the test strip 100 includes at least one electrode used for measuring HCT but not glucose, and at least one electrode used for measuring glucose but not HCT (or likewise for other pairs of analytes). In other aspects, the electrodes 110, 120 are used for measuring both HCT and glucose, either using successive electrical signals for the respective analytes, or using an electrical signal that permits determining both glucose and HCT from measured data corresponding to that electrical signal.

When the resistive component of the blood impedance is in the range of tens of KΩ, parasitic capacitances on the order of fractions of pF on the printed circuit boards in the analytical test meter 180, in the test-strip-receiving module 115, in the test strip 100, and in any other components of the measurement path between the excitation source 181 and the demodulator 182 can affect accuracy and repeatability with which the analyte (blood glucose) can be determined. The effects of the parasitic capacitances can increase in severity as the frequency of measurement signals from excitation source 181 increases.

In order, e.g., to compensate for these effects, the analytical test meter 180 includes a dummy load calibration circuit block 189. In an exemplary embodiment, the dummy load calibration circuit block 189 is electrically connected to the test-strip-receiving module 115 and includes a dummy load 190, e.g., a resistor or a precision resistor (e.g., 22KΩ, 0.1%). The dummy load 190 has selected electrical characteristics, e.g., impedance. The exemplary dummy load calibration circuit block 189 shown also includes the switching unit 191, the couplers 183, 184, the excitation source 181, the demodulator 182, and the processor 186. As discussed above, the excitation source 181 is adapted to selectively provide at least one electrical signal. The demodulator 182 is adapted to produce one or more demodulated signal(s) and the processor 186 is connected to receive the one or more demodulated signal(s) from the demodulator 182. The demodulated signal(s) correspond to the electrical signal(s) from the excitation source 181 and to the electrical properties of the device(s) connected between the excitation source 181 and demodulator 182. In this way, the dummy load circuit block 189 is configured to provide a dummy magnitude correction and a dummy phase correction, and the memory block 149 is configured to store the dummy magnitude correction and the dummy phase correction, e.g., for later use by the processor 186.

A switching unit 191 is adapted to selectively electrically connect the excitation source 181 to the demodulator 182 through either the dummy load 190 or the first and second electrical pins 111, 112 of the test-strip-receiving module 115. In the example shown, the switching unit 191 includes two electrically-controlled single-pole double-throw switches. One of those switches selectively connects the excitation source 181 to one of (a) a first terminal of the dummy load 190 or (b) electrical connector pin 112 (or pin 111) of the test-strip-receiving module 115. The other of the switches selectively connects an input of the demodulator 182 to one of (a) a second terminal of the dummy load 190 or (b) electrical connector pin 111 (or pin 112) of the test-strip-receiving module 115. Other configurations of switches can be used, e.g., a single double-pole double-throw, or an optoelectronic switch or reed relay. The processor 186 can control the switching unit 191 electrically, optically, magnetically, or in other ways.

A storage device 140 in memory block 149 stores data provided by the processor 186, as discussed below. The storage device 140 can include, e.g., a register, memory, delay line, buffer, flip-flop, latch, disk, Flash memory device, or other devices describe below with reference to a storage subsystem 540, FIG. 7.

The processor 186 is adapted to concurrently cause the switching unit 191 to connect through the dummy load 190, cause the excitation source 181 to provide a DC signal (e.g., ground or another 0V reference, or a selected bias), and record first respective value(s) of the demodulated signal(s) from the demodulator 182. The processor 186 then determines a bias of the demodulator 182 using the first respective value(s) and stores the determined bias in the memory block 149, e.g., in the storage device 140. For example, the demodulator 182 can include a transimpedance amplifier and a synchronous demodulator. Applying a DC signal through the dummy load 190 removes time-varying components of the input, so any remaining signal represents bias of the demodulator 182. Saving these values permits correcting for each noted bias. This is discussed further below with reference to step 320, FIG. 4A.

The processor 186 is further adapted to concurrently cause the switching unit 191 to connect through the dummy load 190, cause the excitation source 181 to simultaneously provide both an AC signal and the DC signal, and record second respective value(s) of the demodulated signal(s) from the demodulator 182. From the respective second value(s) and the determined bias of the demodulator, the processor 186 determines a dummy magnitude correction and a dummy phase correction (e.g., phase and gain modifiers of the analytical test meter 180). The processor 186 then stores the determined dummy magnitude correction and the determined dummy phase correction in the memory block 149, e.g., in the storage device 140. For example, the AC admittance of a blood sample is proportional to the hematocrit (HCT) in that sample, so applying an AC input simulates the AC signal used in test conditions. The resulting real and imaginary signals from the demodulator 182 are corrected by subtracting the offset values determined above and stored in the memory block 149, e.g., in the storage device 140. Using the corrected signals and known magnitude and phase characteristics of the dummy load 190, a gain factor and a phase offset are computed and stored.

The processor 186 is further adapted to detect the insertion of the test strip 100 in the test-strip-receiving module 115, as discussed above. The processor 186 can detect insertion at any time, e.g., before applying the DC signal through the dummy load. The processor 186 is adapted to detect the insertion, and then concurrently cause the switching unit 191 to connect through the first and second electrical pins 111, 112, cause the excitation source 181 to simultaneously provide both an AC signal and a DC signal (the same as the previously-applied signal or different), and record third respective value(s) of the demodulated signal(s). The processor 186 then determines phase and gain modifiers of the analytical test meter 180 with the inserted test strip 100 using the third respective value(s), the determined dummy magnitude correction and the determined dummy phase correction (stored in the memory block 149, e.g., in the storage device 140), and the determined bias of the demodulator 182 (also stored in the memory block 149, e.g., in the storage device 140). The processor 186 then stores the determined phase and gain modifiers of the analytical test meter 180 with inserted test strip 100 in the memory block 149, e.g., in the storage device 140.

As a result, calibration values useful for compensating electrical effects of components in the analytical test meter 180 and test strip 100 are stored in the memory block 149, e.g., in the storage device 140, and can be retrieved, as desired. In various embodiments, the processor 186 is further adapted to apply a selected electrical signal across the first and second electrical connector pins 111, 112 (having set switching unit 191 to connect through pins 111, 112) after the test strip 100 is detected. The processor 186 concurrently records fourth respective value(s) of the demodulated signal(s). The processor 186 then determines one or more corrected value(s) corresponding to the fourth respective value(s) using the determined phase and gain modifiers of the analytical test meter 180 with the test strip 100, the determined dummy magnitude correction and the determined dummy phase correction, and the determined bias of the demodulator 182. The processor 186 retrieves these values from the memory block 149, e.g., from the storage device 140. The processor 186 is further adapted to process the determined corrected value(s) to detect presence of the fluid sample and, if the fluid sample is present, determine the analyte.

Figure 2:
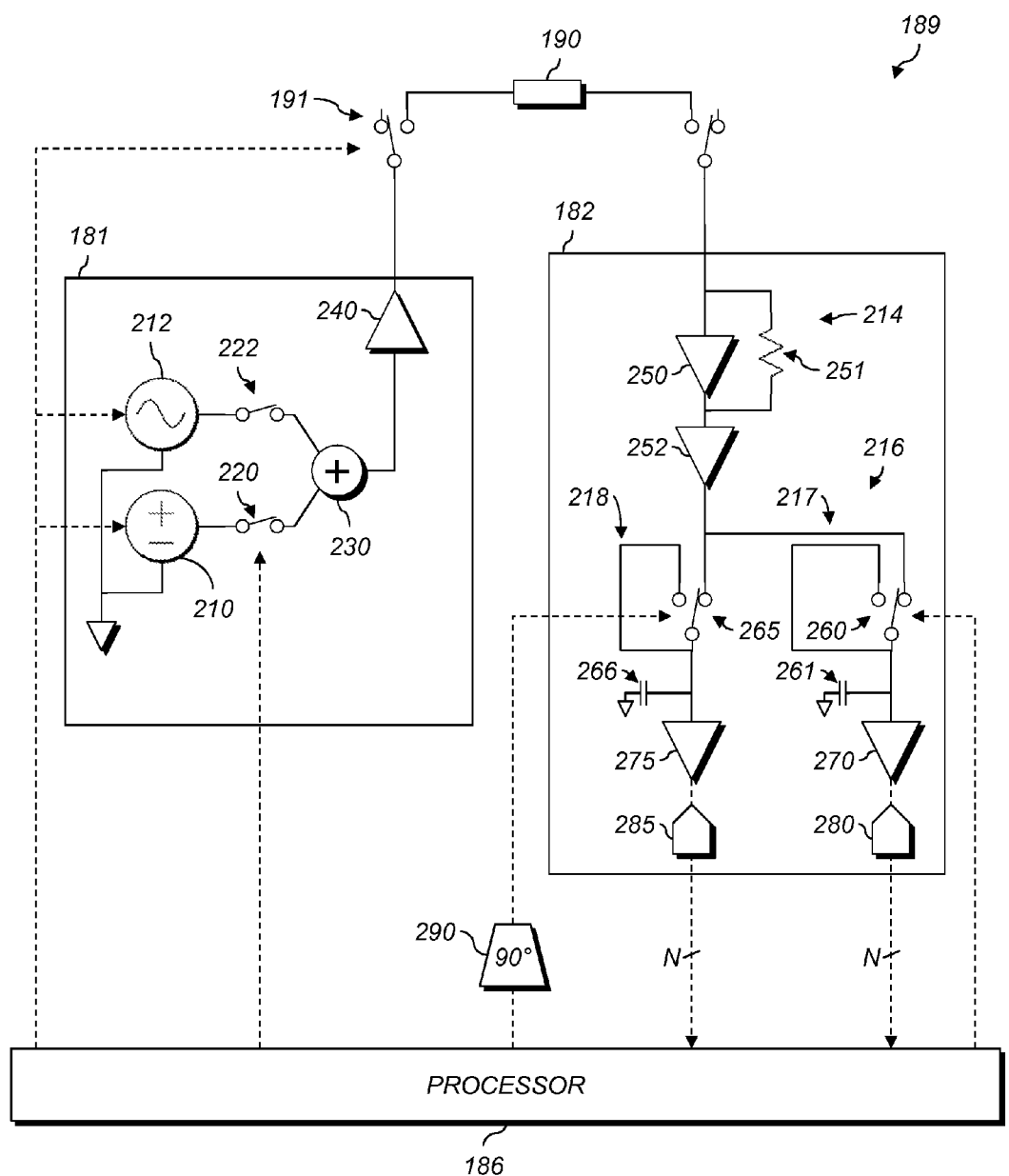
FIG. 2 shows a schematic of an excitation source and a demodulator for use in the exemplary analytical test system of FIG. 1.

FIG. 2 shows a schematic of components of the dummy load calibration circuit block 189, including the excitation source 181 and the demodulator 182, according to various aspects. For clarity, in this example the excitation source 181 and the demodulator 182 are shown connected to only one switch in the switching unit 191 each, so couplers 183, 184, FIG. 1, are not required. Also for clarity, electrical connections carrying control and data signals are shown by dashed lines; electrical connections carrying voltage or current signals are shown by solid lines. Throughout this discussion, any buffer can also be an amplifier, inverting or not, with a desired gain. Filters can also be used along with or in place of buffers to condition signals (e.g., low-pass Butterworth filters). Control arrows pointing at one of two aligned switches indicate control by the processor 186 of both of those switches (e.g., switches 220, 222 and switches 260, 265) with a single or with respective control signals.

The excitation source 181 is configured to provide voltage signals (e.g., AC or DC). In this example, the excitation source 181 includes a DC supply 210 and an AC supply 212. The DC and AC supplies 210, 212 are connected via respective switches 220, 222 to an adder 230, e.g., an op-amp voltage adder. The output of the adder 230 is provided to a buffer 240, which buffers the resulting voltage and sends the buffered voltage to the coupler 183, and subsequently to a switch in the switching unit 191. Other ways of providing voltage signals can be used, including table- or function-driven arbitrary-function or arbitrary-waveform generators (analog or digital); multipliers in place of the switches 220, 222 to multiply the voltages from the DC and AC supplies 210, 212, respectively, by selected weights$\geq 0$; or selective activation or amplitude modulation of the DC and AC supplies 210, 212.

According to this embodiment, the demodulator 182 includes a transimpedance amplifier 214 to measure current(s) and provide corresponding voltage(s). In this example, the transimpedance amplifier 214 includes an op-amp 250 and resistor 251 wired in a transimpedance amplifier configuration well known in the electronics art. For clarity, the second op-amp input is not shown; it can be, e.g., connected to a reference voltage or wired in other ways known in the electronics art for the construction of transimpedance amplifiers. The voltage(s) from the transimpedance amplifier are provided to a demodulation block 216, optionally through a buffer 252.

The demodulation block 216, e.g., a synchronous demodulation block or another appropriate type of demodulation block in demodulator 182, provides demodulated signal(s) using the voltage(s). In various aspects, the demodulation block 216 includes two mixer units 217, 218 driven by respective control signals from the processor 186. Each of the mixer units 217, 218 can include a respective switch 260, 265; a respective filter capacitor 261, 266, which can be part of a low-pass or other filter; and a respective buffer 270, 275 to provide the output of the respective mixer unit 217, 218. Mixer units 217, 218 can mix periodic signals and operate in the frequency domain. Further details of synchronous demodulation according to various aspects are discussed below with reference to FIG. 6.

In various aspects, the switches 260, 265 are analog switches that multiply their control signals with the input signal from buffer 252. In an exemplary embodiment, each control signal is a square wave. In various aspects, the switches 260, 265 have their respective outputs fed back to the one of their inputs not connected to buffer 252. This reduces noise on the outputs of the switches 260, 265.

Other mixer units or demodulators known in the electronics art can also be used. Analog-to-digital converters 280, 285 ("ADCs") can be used to convert the analog voltages from buffers 270, 275 into N-bit digital signals for the processor 186 (e.g., 8-, 10-, 12-, 16-, or 32-bit), or the processor 186 can receive analog inputs and process them in an analog domain or in a digital domain using an internal ADC (not shown).

In various aspects, the processor 186 provides respective control signals to the switches 260 and 265. The respective control signals are 90° out of phase with each other. In this way, the control signal designated as 0° phase can provide a real bias component, and the other control signal can provide an imaginary bias component discussed above. Specifically, in these aspects, the demodulated signal(s) include a real-component signal and an imaginary-component signal. In an example, switch 260 is controlled by the 0° phase control signal to provide the real-component signal. Switch 265 is controlled by the 90° phase control signal to provide the imaginary-component signal.

As a result, the determined bias of the demodulator 182 includes a real bias component and an imaginary bias component. These components correspond respectively to the real-component signal and the imaginary-component signal when the excitation source 181 is providing a DC signal, as described further below with reference to the bias 318, FIG. 4A. The processor 186 is adapted to additively combine (by adding or subtracting) the real bias component and the imaginary bias component with real component(s) and imaginary component(s), respectively, of the second, third, and fourth respective value(s) of the demodulated signal(s) from demodulator 182. As a result, demodulator bias is substantially removed from the respective value(s), advantageously providing improved measurement accuracy.

In various of these aspects, the excitation source 181 provides a first AC signal from the AC supply 212. The analytical test meter 180, FIG. 1, further includes a phase delay unit 290. The phase-delay unit 290 can be included in the processor 186 or otherwise. The phase-delay unit 290 provides a lagged signal 90° in phase behind the first AC signal. (The phase-delay unit 290 can also provide a signal 90° in phase ahead of the first AC signal.) The two mixer units 217, 218 in the demodulator 182 are controlled by the first AC signal (or a signal in phase therewith) and the lagged signal, respectively. The mixer units 217, 218 are thus operative to provide the real-component signal and the imaginary-component signal, respectively.

Figure 3:
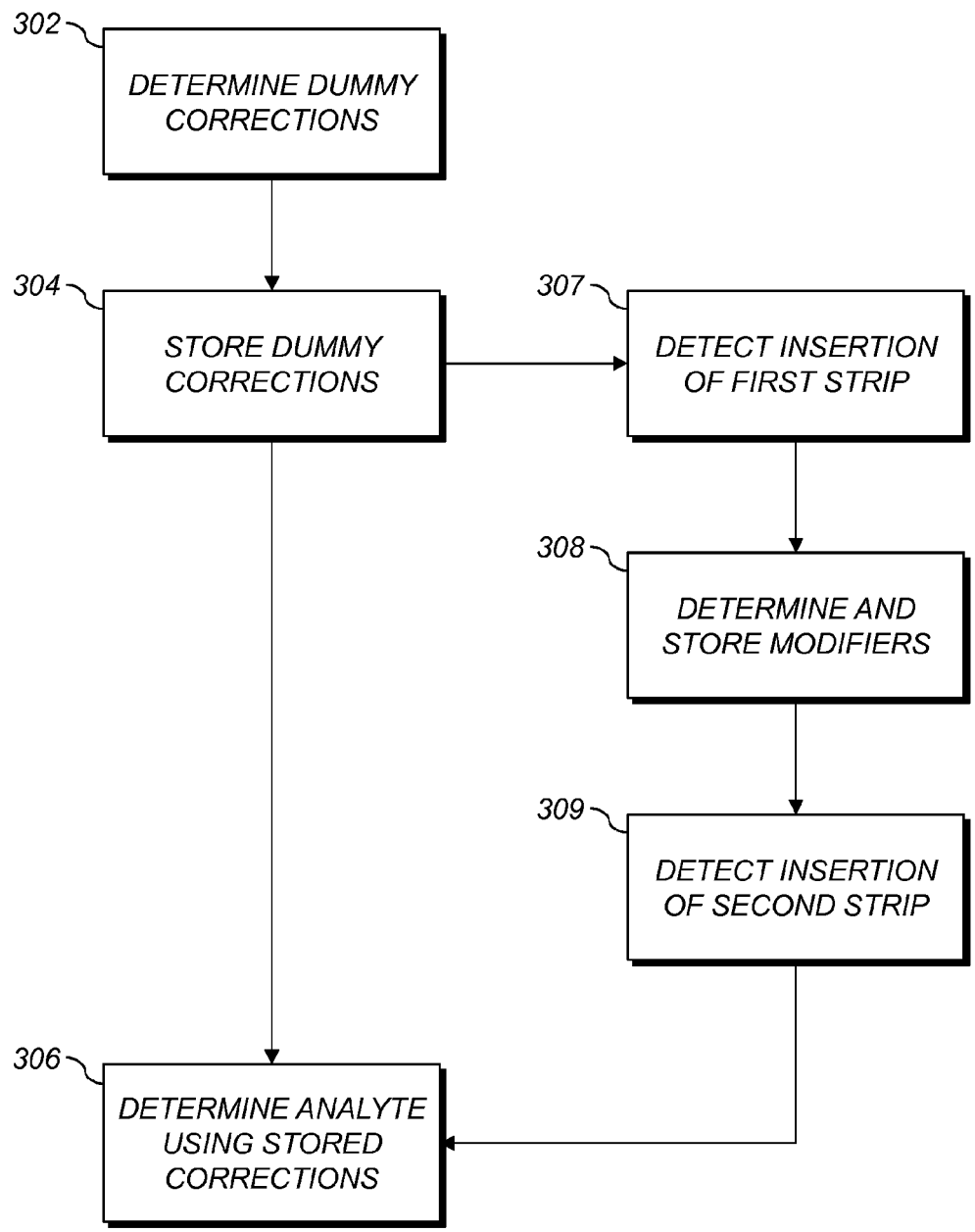
FIG. 3 shows a flowchart illustrating exemplary methods for calibrating an analytical test meter for use with an analytical test strip.

FIG. 3 shows a flowchart illustrating an exemplary method for calibrating an analytical test meter for use with an analytical test strip. In step 302, a dummy magnitude correction and a dummy phase correction of the analytical test meter are determined using a dummy load calibration circuit block of the analytical test meter. In step 304, the determined dummy magnitude correction and the dummy phase correction are stored in a memory block of the analytical test meter (e.g., memory block 140, FIG. 1). In step 306, an analyte is determined using the stored dummy magnitude correction and stored dummy phase correction.

In various aspects, the method further includes performing steps 307, 308, and 309 before the determining-analyte step 306. Steps 307, 308, 309 can be performed, e.g., after step 304, or after step 302, or before either of step 302 or 304, and the execution of steps 302-304 and 307-309 can be interleaved.

In step 307, insertion of a first analytical test strip in a test-strip-receiving module of the portable analytical test meter is detected. This can be as described above, e.g., detecting electrical characteristics, using a sensor, or receiving a user input.

In subsequent step 308, phase and gain modifiers of the portable analytical test meter with the first analytical test strip inserted are determined. The modifiers are then stored, e.g., in memory block 149, FIG. 1. Various aspects of this step are discussed below with reference to modifiers 343.

In subsequent step 309, insertion of a second analytical test strip in the test-strip-receiving module is detected. Step 309 can include detecting removal of the first analytical test strip, or not.

In various aspects using steps 307, 308, 309, the determining-analyte step 306 further includes determining the analyte using the stored phase and gain modifiers of the portable analytical test meter with the first analytical test strip inserted.

In an example, steps 302, 304, 307, and 308 are performed in the factory when the analytical test meter is produced. A typical or representative test strip is inserted and detected in step 307. The resulting values (dummy magnitude correction, dummy phase correction, and phase and gain modifiers) are stored, e.g., in memory block 149. Steps 309 and 306 are performed in the field, i.e., when the user has the meter and wishes to determine an analyte. The user inserts a test strip in the analytical test meter, and that test strip is detected in step 309. The analyte in the fluid sample on the test strip is then determined in step 306 using the values stored at the factory. This advantageously provides more accurate determination of the analyte without requiring that the analytical test meter take time to perform steps 302 and 308 for each test strip.

Figure 4A:
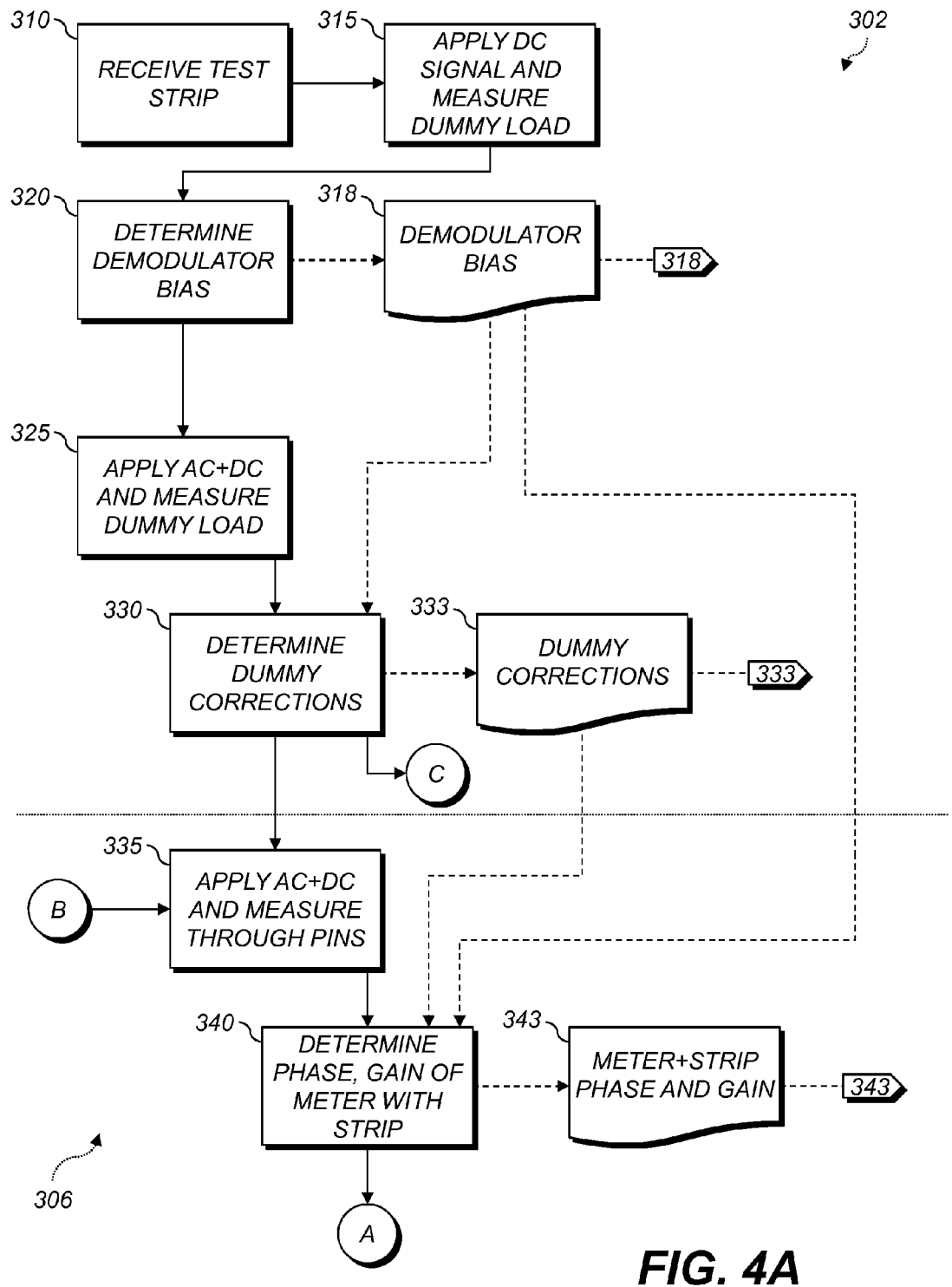
FIGS. 4A and 4B show a flowchart illustrating exemplary methods for determining an analyte in a fluid sample.

In various aspects, steps 302, 304 are performed in the factory; or steps 302, 304, 307, 308 are performed in the factory; or steps 302, 304 are performed in the field; or steps 302, 304, 307, 308 are performed in the field Steps 302, 304, 307, 308 can be performed in the factory and then a repeat measurement check (e.g., of steps 302, 304, or of step 308, or of any of steps 320, 330, or 340, FIG. 4A) can be performed in the field every time a strip is inserted to determine whether the measurement has drifted from the factory calibration parameters.

Figure 4B:
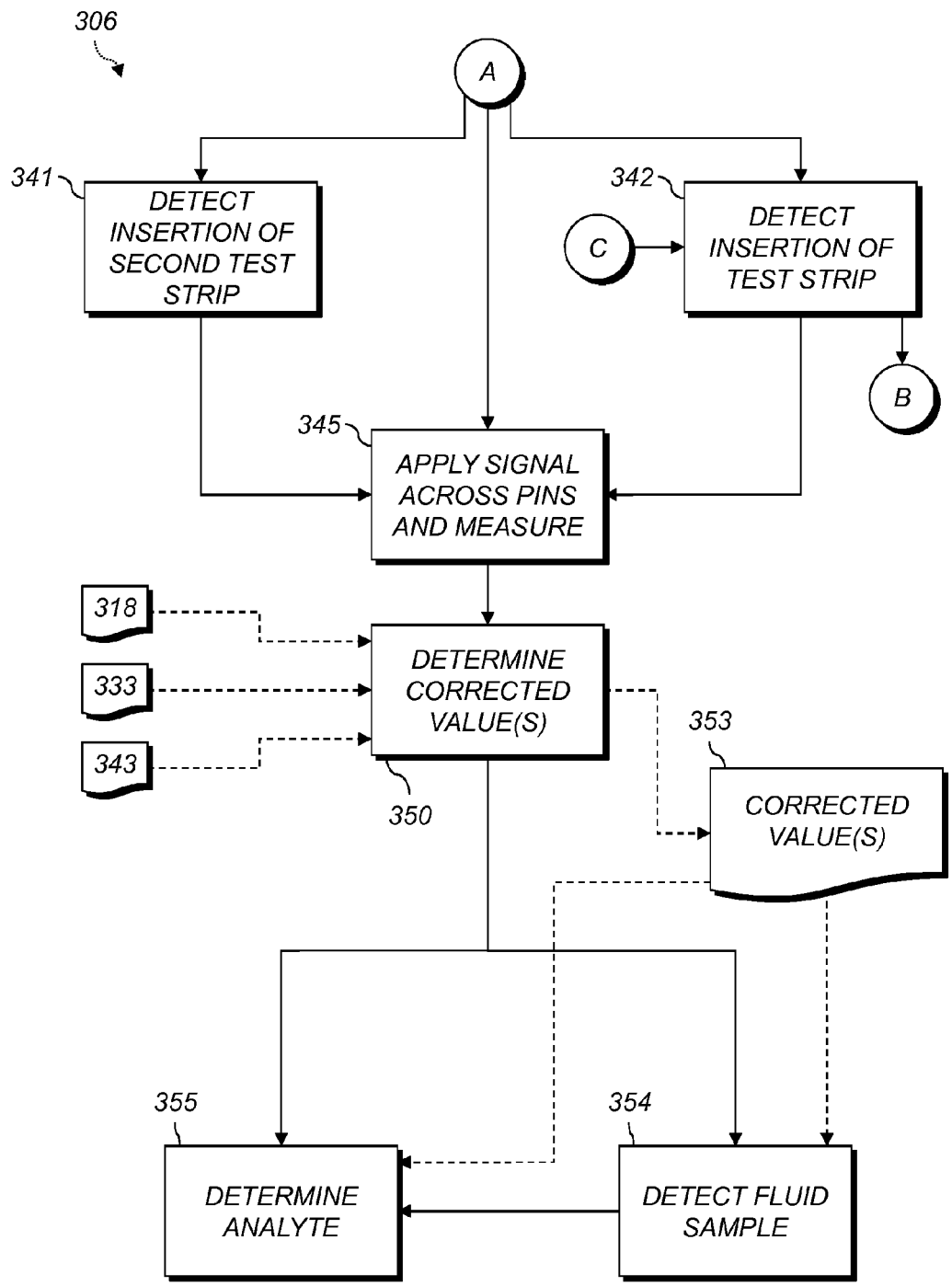

FIGS. 4A and 4B show a flowchart illustrating an exemplary method for determining an analyte in a fluid sample. Also shown are data produced by some of the steps and corresponding dataflow (dashed arrows). The steps can be performed in any order except when otherwise specified, or when data from an earlier step is used in a later step. For purposes of this exemplary method, processing begins with step 310. For clarity of explanation, reference is herein made to various components shown in FIGS. 1 and 2 that can carry out or participate in the steps of the exemplary method. It should be noted, however, that other components can be used; that is, the exemplary method is not limited to being carried out by the identified components. As represented graphically by the horizontal dotted line and the dotted-arrow labels, in an exemplary embodiment steps 310, 315, 320, 335, and 330 are part of step 302, FIG. 3; and steps 335, 340, 342, 345, 350, 354, 355 are part of step 306.

In step 310, an analytical test strip is received. The test strip 100 is received upon insertion thereof into a test-strip-receiving module 115 of an analytical test meter 180 so that first and second electrical contact pads 101, 102 exposed on the test strip 100 electrically contact first and second electrical connector pins 111, 112 of the test-strip-receiving module 115, respectively. The test strip 100 includes a sample-receiving chamber 130 adapted to receive the fluid sample. The sample-receiving chamber 130 is electrically connected between the first and second electrical contact pads 101, 102. In an example, step 315 is next. In another example, this step is not performed; instead, step 342 (discussed below) is performed before step 335. In yet another example, processing begins with step 315, and step 310 is performed before step 335.

In step 315, using an electronics module (e.g., excitation source 181) of the analytical test meter 180, a DC signal is applied through a dummy load to a demodulator 182 that produces demodulated signal(s). The demodulated signal(s) can include a real-component signal and an imaginary-component signal. Here and throughout this disclosure, DC signals can have ripple and noise; it is not required that any DC signal be perfectly and exactly at one voltage, unvarying with time. Concurrently with the application of the DC signal, first respective value(s) of the demodulated signal(s) are recorded. Recording can be performed by the electronics module, a processor 186 of the analytical test meter 180, or other devices in the analytical test meter 180. Step 320 is next.

In step 320, using the processor of the analytical test meter 180, a bias 318 of the demodulator is automatically determined using the first respective value(s). This processing can be performed by one processing resource or multiple processing resources; processing resources can include hardware devices, firmware, or software programs executed on processors. In an example, the test meter includes a digital signal processor or other processing chip (e.g., processor 186). In various versions, step 320 further includes storing the recorded first value (i.e., the one of the recorded first respective value(s)) corresponding to the real-component signal as a real bias value and the recorded first value corresponding to the imaginary-component signal as an imaginary bias value.

The determined bias 318 of the demodulator 182 thus includes the first bias value and the second bias value. Step 325 is next.

In an exemplary aspect, the demodulator 182 includes at least one operational amplifier (op amp) AC-coupled to a signal passed via switching unit 191. As a result, substantially no DC component is measured. The op amps can be biased by a reference voltage and thus operate with a dc offset, or otherwise. Since substantially no DC component is measured, and the DC signal has no substantially AC component, the first respective value(s) substantially correspond to offsets of the measurement circuitry in the demodulator and not to properties of the DC signal. Measuring the bias 318 thus advantageously permits correcting for offsets in the demodulator 182 that might otherwise carry forward as errors in measurements of the analyte.

In step 325, using the electronics module, a DC signal and an AC signal are simultaneously applied through dummy load 190 to the demodulator 182. Here and throughout this disclosure, AC signals can be sinusoidal or not. For example, AC signals can be square waves or approximations of sinusoids formed by low-pass filtering square waves. Concurrently with the application of the signals, second respective value(s) of the demodulated signal(s) are recorded. Step 330 is next.

In step 330, using the processor 186, dummy corrections 333 are automatically determined using the respective second value(s) and the determined bias 318 of the demodulator 182. The dummy corrections 333 include a dummy phase correction and a dummy magnitude correction. For example, the second value(s) can be adjusted according to the determined bias 318 of the demodulator 182, and the dummy corrections 333 of the analytical test meter can be determined using the adjusted second value(s). In aspects using real and imaginary components, step 330 can include additively combining the real and imaginary bias values from bias 318 with the second value(s) before determining the dummy corrections 333. The dummy corrections 333 can include phase and gain modifiers of the analytical test meter 180. Step 335 is next.

In step 335, after receiving step 310 (or, in various aspects, after detecting step 342, discussed below), using the electronics module, the DC signal and an AC signal are simultaneously applied through the first and second electrical pins to the demodulator 182. Third respective value(s) of the demodulated signal(s) as measured through the electrical pins 111, 112 are concurrently recorded. Step 340 is next.

In step 340, using the processor 186, phase and gain modifiers 343 of the analytical test meter 180 with inserted test strip 100 are automatically determined using the third respective value(s), the determined dummy corrections 333 of the analytical test meter 180, and the determined bias 318 of the demodulator 182. In various embodiments, step 340 includes automatically operating a switching unit 191 to direct the DC signal and the AC signal to the first electrical pin 111 and to connect the second electrical pin 112 to an input of the demodulator 182. In aspects using real and imaginary components, step 340 can include additively combining the real and imaginary bias values from bias 318 with the third value(s) before determining modifiers 343. Step 340 can also include adjusting the third value(s) according to the determined dummy corrections 333 before determining modifiers 343. Step 345 or, in various embodiments, step 341 or step 342 is next. In an example, steps 315, 320, 325, 330, 335, 340, 345, 350 are performed in that order. In another example, steps 315, 320, 325, 330, 342, 335, 340, 345, 350 are performed in that order.

In step 342, the insertion of the test strip 100 is automatically detected. In response to the detection, a selected electrical signal is applied in step 345. In various aspects, steps 315, 320, 325, and 330 are performed before the test strip 100 is received (step 310) and insertion of the test strip 100 is detected (this step 342). In these aspects, the bias 318 and the dummy corrections 333 can be determined before a test strip 100 is inserted, and the stored values of the bias 318 and the dummy corrections 333 can be used to determine modifiers 343 and perform other computations (e.g., as in step 350) with respect to multiple test strips 100. In other aspects, steps 315, 320, 325, and 330 to re-determine the bias 318 and the dummy corrections 333 are carried out for each test strip 100, e.g., upon detection of the insertion of the test strip 100. Step 342 can also be performed before step 335. In an example, the bias 318 and the dummy corrections 333 are to be determined after the detection, and step 342 is followed by Step 315. In another example, the bias 318 and the dummy corrections 333 have been determined before the detection, and step 342 is followed by step 345.

In step 345, using the processor 186, a selected electrical signal is automatically applied across the first and second electrical connector pins 111, 112 after the test strip 100 is received (step 310) or detected (step 342). The processor 186 can direct the electronics module to produce the signal, or produce it directly. The signal can be substantially the same as the AC and DC combined signal applied in step 340, FIG. 4A; the selected electrical signal can include the DC signal and the AC signal applied in step 335 of measuring through the first and second electrical pins 111, 112. Concurrently, fourth respective value(s) of the demodulated signal(s) are measured. Step 345 can also be performed after a fluid sample has been detected, e.g., electrically or via a user input control. Step 350 is next.

In step 350, using the processor 186, one or more corrected value(s) 353 corresponding to the fourth respective value(s) are automatically determined. The processor 186 determines the corrected value(s) using the determined phase and gain modifiers 343 of the analytical test meter 180 with test strip 100, the determined dummy corrections 333, and the determined bias 318 of the demodulator 182. Step 355 is next, or, in various aspects, step 354.

In various aspects, in step 354, the corrected value(s) 353 are automatically processed, e.g., using the processor 186, to detect whether the fluid sample applied to the test strip 100 has filled the sample-receiving chamber 130. This detection can be done, e.g., by applying current and measuring voltage as described above or by monitoring the value(s) of the demodulated signal(s) for a decrease in impedance. The demodulated signal(s) can be transimpedance-amplifier output signals or other signals indicative of current, and an increase in the corrected value(s) corresponding to those signal(s) over time can indicate the sample-receiving chamber 130 has filled so is conductive. Step 355 is next.

In step 355, the processor 186 automatically processes the corrected value(s) 353 to determine the analyte in the applied fluid sample. This can be as discussed above.

In an example, step 341 is used. Steps 315, 320, 325, 330, 342, 335, and 340 are performed, and resulting values are stored. These steps can be performed, e.g., in the factory when the analytical test meter is produced. In this example, step 340 is followed by step 341. Steps 341, 345, 350, 354, and 355 can be performed in the field when the user inserts a test strip into the analytical test meter, as discussed above with reference to FIG. 3.

In step 341, the processor detects the insertion of a second test strip in the test-strip-receiving module. This can be as discussed above with reference to step 309, FIG. 3. Step 341 is followed by step 345.

In step 345, a selected electrical signal is applied across the first and second electrical connector pins after the second test strip is detected. Fourth respective value(s) of the demodulated signal(s) are concurrently recorded. This can be as discussed above.

In subsequent step 350, one or more corrected value(s) corresponding to the fourth respective value(s) are determined. This determination is made using the stored determined phase and gain modifiers 343 of the portable analytical test meter with test strip, the stored determined dummy magnitude correction, the stored determined dummy phase correction (both from the dummy corrections 333), and the stored determined bias 318 of the demodulator. This can be done as discussed above. Step 350 can be followed by step 354 or step 355.

In step 354, the corrected value(s) are processed to detect presence of the fluid sample on the second test strip. If the fluid sample is present, or if step 354 is not used, in step 355, the analyte is determined.

In an example, the analytical test meter 180 includes a transimpedance amplifier 214 and a synchronous demodulator (e.g., demodulation block 216) similar to those shown in demodulator 182, FIG. 2. The AC signal of steps 325, 335, and 345 is a square wave filtered through a fourth-order Butterworth filter. The demodulator 182 is driven with 0°- and 90°-phase signals to produce real-component signals and imaginary-component signals. The determined bias 318 of the demodulator 182 includes real and imaginary bias values BR, BI, as discussed above. Each of the foregoing values can be stored. In steps 330, 340, and 350, the real and imaginary bias values BR, BI are subtracted from the corresponding values(s) of the demodulated signal(s).

In this example, step 325 includes measuring real and imaginary values of the demodulated signal(s), denoted MR and MI. Step 330 includes forming bias-corrected values $$CR=MR-BR; CI=MI-BI. \quad (1)$$

Step 330 also includes receiving a known magnitude DM and phase DP of dummy load 190. DM and DP can be stored in the memory block 149, e.g., in the storage device 140, FIG. 1, and can be programmed into the memory block 149, e.g., into the storage device 140, before the analytical test meter 180, FIG. 1, is shipped. DM and DP can be the same for all analytical test meters 180, or can be determined, e.g., per meter or per lot of meters. Step 330 includes computing a magnitude and phase CM, CP of the bias-corrected values as known in the mathematical art:

$$\mathrm{Mag}(r,i)=\sqrt{r^2+i^2}; Ph(r,i)=a\tan 2(r,i) \quad (2)$$

$$CM=\mathrm{Mag}(CR,CI); CP=Ph(CR,CI) \quad (3)$$

where a tan 2( ) is the four-quadrant arc-tangent. Step 330 further includes computing the dummy phase correction (AP) and dummy magnitude (gain) correction (AG). Together, these values are the dummy corrections 333. The AP and values AG values can be stored, e.g., in step 304, FIG. 3. The computation is:

$$AP=CP-DP \quad (4)$$

$$AG=CM\cdot DM \quad (5)$$

Continuing this example, step 340 includes measuring MR and MI values, forming CR and CI values per (1), and computing CM and CP values per (3). The CM and CP values are then corrected using the dummy corrections 333 to form corrected values OM, OP:

$$OM=AG/CM \quad (6)$$

$$OP=CP-AP \quad (7)$$

Real and imaginary components OR, OI can be determined as $$OR=OM\cos(OP); OI=OM\sin(OP). \quad (8)$$

The OM and OP values are phase and gain modifiers 343 of the analytical test meter with test strip and can be stored. In various configurations, OM and OP represent a complex impedance in parallel with the fluid sample to be measured.

In this example, step 350 includes determining corrected value(s) for the fourth respective value(s). Stored BR, BI, AG, AP, OM, and OP values are received. For real and imaginary values FMR, FMI in the fourth respective value(s), computations are carried out as described above:

$$FCR=FMR-BR \quad (9)$$

$$FCI=FMI-BI \quad (10)$$

$$FCM=\mathrm{Mag}(FCR,FCI); FCP=Ph(FCR,FCI) \quad (11)$$

$$FOM=AG/FCM \quad (12)$$

$$FOP=FCP-AP \quad (13)$$

$$FOR=FOM\cos(FOP); FOI=FOM\sin(FOP). \quad (14)$$

Product terms PM, PP and difference terms SM, SP are then determined:

$$PM=OM\cdot FOM \quad (15)$$

$$PP=OP+FOP \quad (16)$$

$$SM=\mathrm{Mag}(OR-FOR,OI-FOI) \quad (17)$$

$$SP=Ph(OR-FOR,OI-FOI). \quad (18)$$

Using those terms, the corrected value(s) ZM, ZP are computed:

$$ZM=PM/SM \quad (19)$$

$$ZP=PP-SP \quad (20)$$

These corrected values can then be processed (step 355) to determine the analyte. In various configurations, these computations remove the previously-measured parasitic (OM and OP) from the measurement of parasitic in parallel with fluid sample (FOM and FOP) to determine the properties of the fluid sample alone (ZM and ZP).

Figure 5:
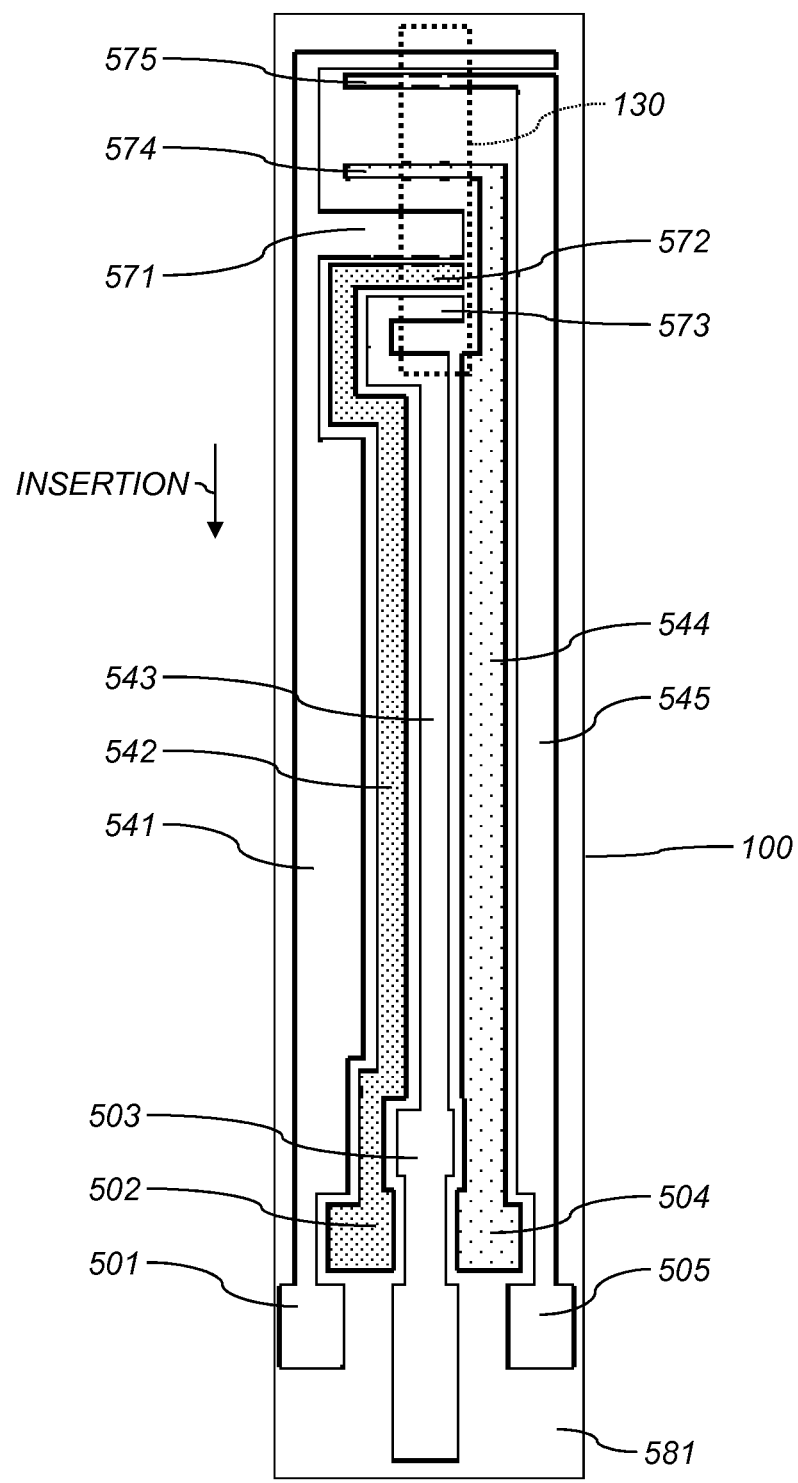
FIG. 5 is a plan view of an exemplary test strip.

FIG. 5 is a plan view of an exemplary test strip 100. The test strip 100 has a planar design (e.g., using 2D printed conductive tracks 541, 542, 543, 544, 545) rather than co-facial (opposing faces). The sample-receiving chamber 130 (dotted outline) is defined by a spacer (not shown) and covered with top tape (not shown). The test strip 100 includes a plurality of conductive tracks 541, 542, 543, 544, 545 electrically discontinuous from each other. Each of the conductive tracks 541, 542, 543, 544, 545 connects a respective contact pad 501, 502, 503, 504, 505 to a respective electrode 571, 572, 573, 574, 575. The conductive tracks 542, 544 and their corresponding contact pads 502, 504 and electrodes 572, 574 are shown hatched only to permit visually distinguishing the various conductive tracks from each other. The electrodes 571, 572, 573, 574, 575, contact pads 501, 502, 503, 504, 505, and conductive tracks 541, 542, 543, 544, 545 can be printed from a conductive material, e.g., carbon, in a single printing operation, or can be fabricated in other ways (e.g., silk-screening).

Each electrode 571, 572, 573, 574, 575 is arranged at least partially on a first side 581 of the test strip 100, and is and at least partially adjacent to the sample-receiving chamber 130.

That is, each electrode 571, 572, 573, 574, 575 is arranged so that the electrical properties of that electrode or its corresponding conductive track can be influenced by a sample in the sample-receiving chamber 130, or so that electrical signals through the respective conductive track 541, 542, 543, 544, 545 can be applied to a sample in the sample-receiving chamber 130. Each conductive track 541, 542, 543, 544, 545 can be adjacent to the sample-receiving chamber 130 on any side thereof, or more than one side thereof. The test strip 100 can also include other conductive tracks (not shown) that are not necessarily adjacent to the sample-receiving chamber 130. In an example, an enzyme is deposited in an enzyme area overlapping the electrodes 571, 572, 573 but not overlapping electrodes 574, 575.

Figure 6:
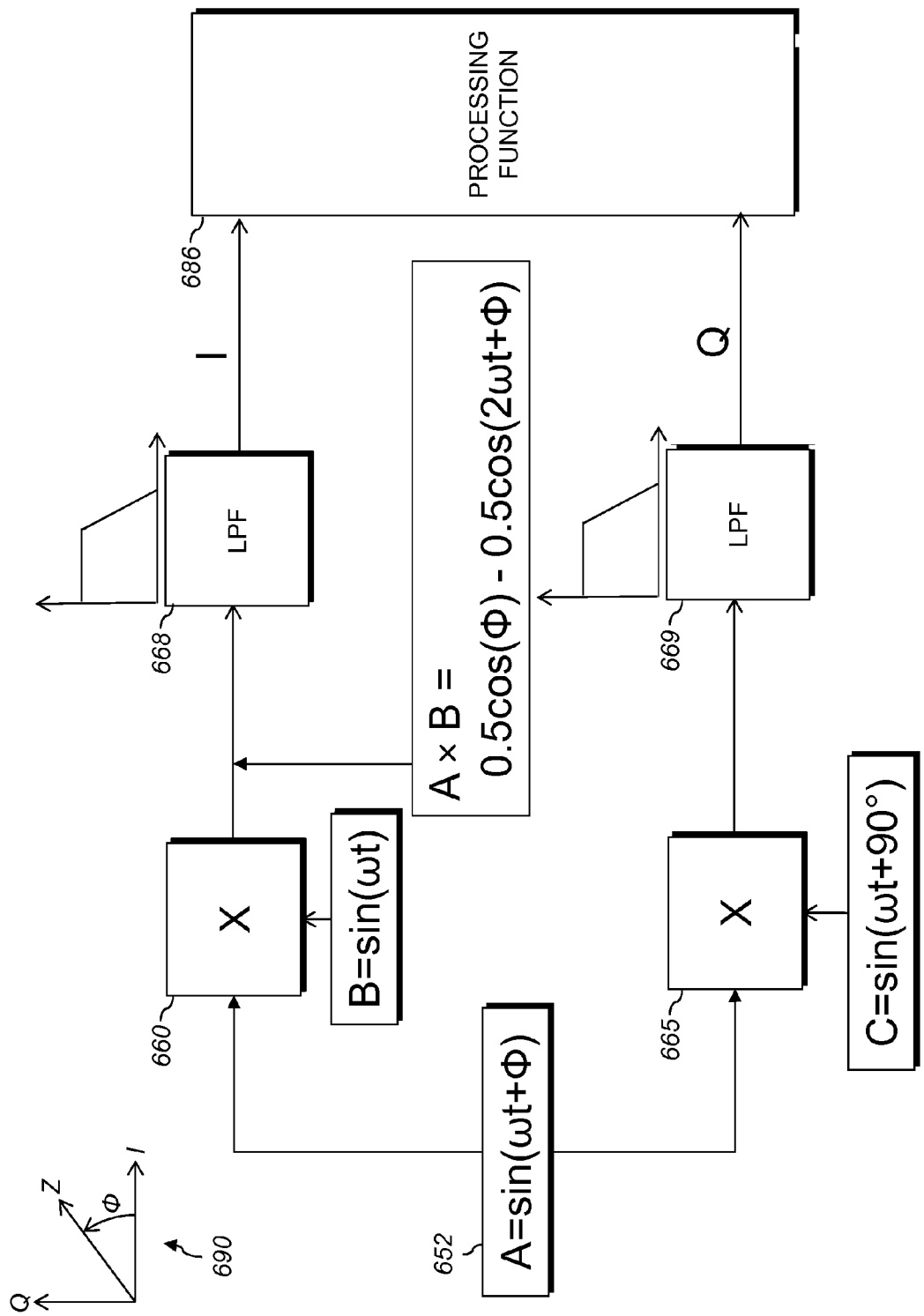
FIG. 6 is a dataflow diagram of an example of synchronous demodulation.

FIG. 6 shows a dataflow diagram of an example of synchronous demodulation. The multipliers 660, 665 take as input a signal $A=\sin(\omega t+\phi)$. This can be, e.g., a signal from buffer 252, FIG. 2. The $\omega t$ term can represent a frequency of an excitation signal provided by excitation source 181, FIG. 2. The $\phi$ term can represent a phase shift introduced by sample-receiving chamber 130, FIG. 1, or a fluid sample therein. The $\phi$ term can also represent an overall phase shift between the excitation source 181 and the demodulator 182, FIG. 1.

The multiplier 660 multiplies A by a known signal $B=\sin(\omega t)$. This can be a control signal from processor 186, FIG. 2. Signal B can be the fundamental frequency in a square wave. When a square wave is used, all odd harmonics of signal B are also multiplied with signal A by the multiplier 660. The multiplier 660 can include a switch that switches signal A and is controlled by signal B, e.g., switch 260, FIG. 2. Various mixing units, including some using switches, are discussed in ANALOG DEVICES tutorial MT-080 "Mixers and Modulators," October 2008, incorporated herein by reference.

The output of the multiplier 660 is an intermediate signal $$0.5\cos(\phi)-0.5\cos(2\omega t+\phi).$$

This signal is filtered by the low-pass filter 668 to retain substantially only the DC component. That is, the $\cos(2\omega t+\phi)$ term is removed from the intermediate signal, leaving only a DC signal with the value $$0.5\cos(\phi).$$

This is a DC (substantially non-time-varying) value since it does not depend on the value of t. The low-pass filter 668 can include capacitor 261, FIG. 2. Odd harmonics introduced if signal B is a square wave can be filtered out by the low-pass filter 668. The resulting DC component is an in-phase (or "real") component I.

Similarly, the multiplier 665 multiplies signal A by a signal $C=\sin(\omega t+90°)$, i.e., 90° out of phase with signal B. The multiplier 665 can include a switch that switches signal A and is controlled by signal C, e.g., switch 265, FIG. 2. The multiplier 665 produces an intermediate signal which is filtered by the low-pass filter 669. The low-pass filter 668 can include capacitor 266, FIG. 2. The resulting DC component is a quadrature (or "imaginary") component Q.

The in-phase and quadrature components are then provided to processing function 686. Processing function 686 can be a mathematical function, and can be implemented as part of processor 186, FIG. 1, as a program running on processor 186, or using dedicated hardware communicatively connected with processor 186. The processing function 686 can, e.g., compute magnitudes or phases per Eq. (2), above. The r and i parameters in Eq. (2) stand for "real" and "imaginary;" the in-phase component from low-pass filter 668 can be used for r and the quadrature component from low-pass filter 669 can be used for i. In various aspects, phase is computed and is used to determine Hct. In various aspects, magnitude is computed and is used to determine Hct. Further examples are given in U.S. application Ser. No. 13/857,280, incorporated herein by reference. Plot 690 shows an example of a signal Z with phase $\phi$ plotted on an in-phase axis I and a quadrature axis Q, In view of the foregoing, various aspects or embodiments process measured data to correct for errors that may be introduced by parasitic electrical properties of the test meter or test strip. A technical effect of various aspects is to provide improved measurement of hematocrit, and thus of blood glucose, permitting improved dosing of insulin to diabetic patients.

Throughout this description, some aspects are described in terms that would ordinarily be implemented as software programs. Those skilled in the art will readily recognize that the equivalent of such software can also be constructed in hardware (hard-wired or programmable), firmware, or microcode. Accordingly, aspects of the present invention may take the form of an entirely hardware embodiment, an entirely software embodiment (including firmware, resident software, or micro-code), or an embodiment combining software and hardware aspects. Software, hardware, and combinations can all generally be referred to herein as a "service," "circuit," "circuitry," "module," or "system." Various aspects can be embodied as systems, methods, or computer program products. Because data manipulation algorithms and systems are well known, the present description is directed in particular to algorithms and systems forming part of, or cooperating more directly with, systems and methods described herein. Other aspects of such algorithms and systems, and hardware or software for producing and otherwise processing signals or data involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Figure 7:
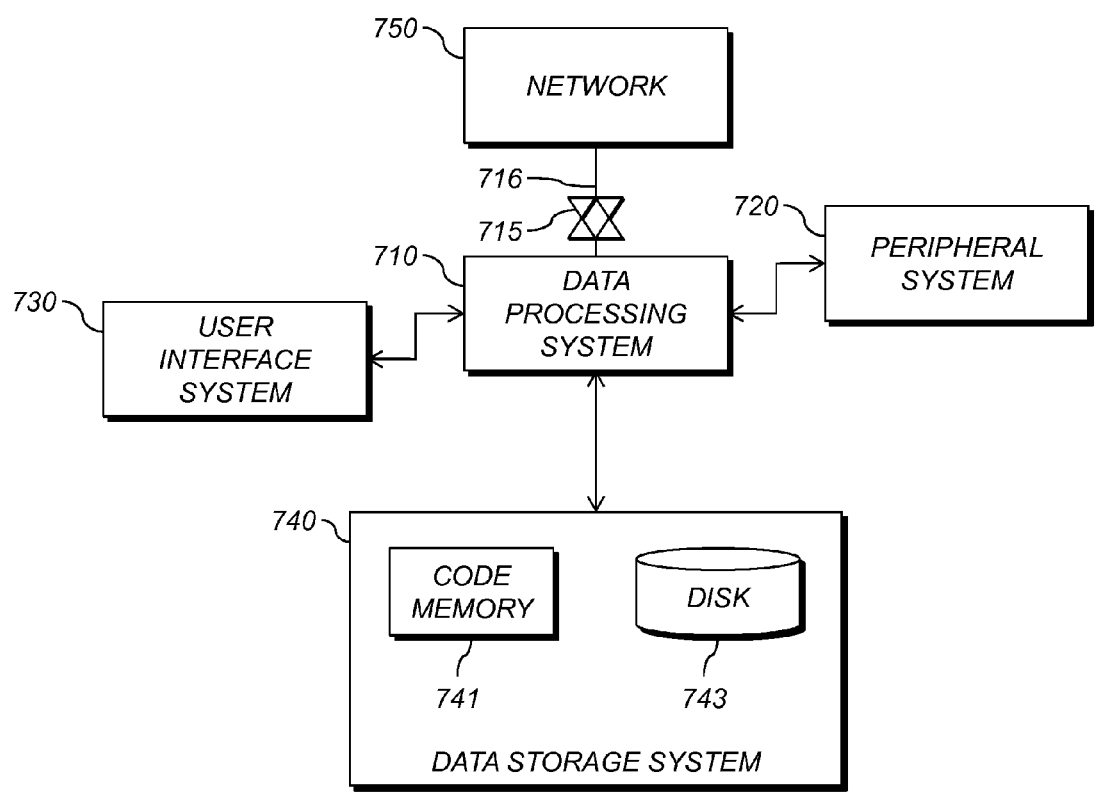
FIG. 7 is a high-level diagram showing components of a data-processing system.

FIG. 7 is a high-level diagram showing the components of an exemplary data-processing system for analyzing data and performing other analyses described herein. The system includes a data processing system 710, a peripheral system 720, a user interface system 730, and a data storage system 740. The peripheral system 720, the user interface system 730 and the data storage system 740 are communicatively connected to the data processing system 710. Data processing system 710 can be communicatively connected to network 750, e.g., the Internet or an X.25 network, as discussed below. The processor 186, FIG. 1, can include or communicate with one or more of systems 710, 720, 730, 740, and can each connect to one or more network(s) 750.

The data processing system 710 includes one or more data processor(s) that implement processes of various aspects described herein. A "data processor" is a device for automatically operating on data and can include a central processing unit (CPU), a desktop computer, a laptop computer, a mainframe computer, a personal digital assistant, a digital camera, a cellular phone, a smartphone, or any other device for processing data, managing data, or handling data, whether implemented with electrical, magnetic, optical, biological components, or otherwise.

The phrase "communicatively connected" includes any type of connection, wired or wireless, between devices, data processors, or programs in which data can be communicated. Subsystems such as peripheral system 720, user interface system 730, and data storage system 740 are shown separately from the data processing system 710 but can be stored completely or partially within the data processing system 710.

The data storage system 740 includes or is communicatively connected with one or more tangible non-transitory computer-readable storage medium(s) configured to store information, including the information needed to execute processes according to various aspects. A "tangible non-transitory computer-readable storage medium" as used herein refers to any non-transitory device or article of manufacture that participates in storing instructions which may be provided to processor 186 for execution. Such a non-transitory medium can be non-volatile or volatile. Examples of non-volatile media include floppy disks, flexible, disks, or other portable computer diskettes, hard disks, magnetic tape or other magnetic media, Compact Discs and compact-disc read-only memory (CD-ROM), DVDs, BLU-RAY disks, HD-DVD disks, other optical storage media, Flash memories, read-only memories (ROM), and erasable programmable read-only memories (EPROM or EEPROM). Examples of volatile media include dynamic memory, such as registers and random access memories (RAM). Storage media can store data electronically, magnetically, optically, chemically, mechanically, or otherwise, and can include electronic, magnetic, optical, electromagnetic, infrared, or semiconductor components.

Aspects of the present invention can take the form of a computer program product embodied in one or more tangible non-transitory computer readable medium(s) having computer readable program code embodied thereon. Such medium(s) can be manufactured as is conventional for such articles, e.g., by pressing a CD-ROM. The program embodied in the medium(s) includes computer program instructions that can direct data processing system 710 to perform a particular series of operational steps when loaded, thereby implementing functions or acts specified herein.

In an example, data storage system 740 includes code memory 741, e.g., a random-access memory, and disk 743, e.g., a tangible computer-readable rotational storage device such as a hard drive. Computer program instructions are read into code memory 741 from disk 743, or a wireless, wired, optical fiber, or other connection. Data processing system 710 then executes one or more sequences of the computer program instructions loaded into code memory 741, as a result performing process steps described herein. In this way, data processing system 710 carries out a computer implemented process. For example, blocks of the flowchart illustrations or block diagrams herein, and combinations of those, can be implemented by computer program instructions. Code memory 741 can also store data, or not: data processing system 710 can include Harvard-architecture components, modified-Harvard-architecture components, or Von-Neumann-architecture components.

Computer program code can be written in any combination of one or more programming languages, e.g., JAVA, Smalltalk, C++, C, or an appropriate assembly language. Program code to carry out methods described herein can execute entirely on a single data processing system 710 or on multiple communicatively-connected data processing systems 710. For example, code can execute wholly or partly on a user's computer and wholly or partly on a remote computer or server. The server can be connected to the user's computer through network 750.

The peripheral system 720 can include one or more devices configured to provide digital content records to the data processing system 710. For example, the peripheral system 720 can include digital still cameras, digital video cameras, cellular phones, or other data processors. The data processing system 710, upon receipt of digital content records from a device in the peripheral system 720, can store such digital content records in the data storage system 740.

The user interface system 730 can include a mouse, a keyboard, another computer (connected, e.g., via a network or a null-modern cable), or any device or combination of devices from which data is input to the data processing system 710. In this regard, although the peripheral system 720 is shown separately from the user interface system 730, the peripheral system 720 can be included as part of the user interface system 730.

The user interface system 730 also can include a display device, a processor-accessible memory, or any device or combination of devices to which data is output by the data processing system 710. In this regard, if the user interface system 730 includes a processor-accessible memory, such memory can be part of the data storage system 740 even though the user interface system 730 and the data storage system 740 are shown separately in FIG. 7.

In various aspects, data processing system 710 includes communication interface 715 that is coupled via network link 716 to network 750. For example, communication interface 715 can be an integrated services digital network (ISDN) card or a modem to provide a data communication connection to a corresponding type of telephone line. As another example, communication interface 715 can be a network card to provide a data communication connection to a compatible local-area network (LAN), e.g., an Ethernet LAN, or wide-area network (WAN). Wireless links, e.g., WiFi or GSM, can also be used. Communication interface 715 sends and receives electrical, electromagnetic or optical signals that carry digital data streams representing various types of information across network link 716 to network 750. Network link 716 can be connected to network 750 via a switch, gateway, hub, router, or other networking device.

Network link 716 can provide data communication through one or more networks to other data devices. For example, network link 716 can provide a connection through a local network to a host computer or to data equipment operated by an Internet Service Provider (ISP).

Data processing system 710 can send messages and receive data, including program code, through network 750, network link 716 and communication interface 715. For example, a server can store requested code for an application program (e.g., a JAVA applet) on a tangible non-volatile computer-readable storage medium to which it is connected. The server can retrieve the code from the medium and transmit it through the Internet, thence a local ISP, thence a local network, thence communication interface 715. The received code can be executed by data processing system 710 as it is received, or stored in data storage system 740 for later execution.

PARTS LIST FOR FIGS. 1-7

100 test strip
101, 102 contact pads
110 electrode
111, 112 connector pins
115 test-strip-receiving module
116, 117 conductors
120 electrode
130 sample-receiving chamber
140 storage device
149 memory block
150 electrode 151 conductor
155 electrode
156 conductor
169 output unit
180 analytical test meter
181 excitation source
182 demodulator
183, 184 couplers
186 processor
189 dummy load calibration circuit block
190 dummy load
191 switching unit
210 DC supply
212 AC supply
214 transimpedance amplifier
216 demodulation block
217, 218 mixer units
220, 222 switches
230 adder
240 buffer
250 op-amp
251 resistor
252 buffer
260 switch
261 capacitor
265 switch
266 capacitor
270, 275 buffer
280, 285 analog-to-digital (ADC) converter
290 phase-delay unit
302, 304, 306 steps
307, 308, 309 steps
310, 315 steps
318 demodulator bias
320, 325, 330 steps
333 dummy corrections
335, 340, 341, 342 steps
343 phase and gain modifiers
345, 350 steps
350 step
353 corrected value(s)
354, 355 steps
501, 502, 503, 504, 505 contact pads
541, 542, 543, 544, 545 conductive tracks
571, 572, 573, 574, 575 electrodes
581 side
660, 665 multipliers
668, 669 low-pass filters
686 processing function
690 plot
710 data processing system
715 communication interface
716 network link
720 peripheral system
730 user interface system
740 data storage system
741 code memory
743 disk
750 network The invention is inclusive of combinations of the aspects described herein. References to "a particular aspect" (or "embodiment" or "version") and the like refer to features that are present in at least one aspect of the invention. Separate references to "an aspect" or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

The invention claimed is:

1. A portable analytical test meter for use with an associated analytical test strip, the portable analytical test meter comprising:
   a) a test-strip-receiving module adapted to receive the analytical test strip;
   b) a dummy load calibration circuit block electrically connected to the test-strip-receiving module; and
   c) a memory block;
   d) wherein the dummy load circuit block is configured to provide a dummy magnitude correction and a dummy phase correction; and
   e) wherein the memory block is configured to store the dummy magnitude correction and the dummy phase correction,
   wherein the analytical test strip includes an analyte chamber and wherein:
   a1) the test-strip-receiving module includes first and second electrical connector pins;
   b1) the dummy load calibration circuit block includes:
      i) a dummy load having selected electrical characteristics;
      ii) an excitation source adapted to selectively provide at least one electrical signal;
      iii) a demodulator adapted to produce one or more demodulated signal(s);
      iv) a processor connected to receive the one or more demodulated signal(s) from the demodulator; and
      v) a switching unit adapted to selectively electrically connect the excitation source to the demodulator through either the dummy load or the first and second electrical pins of the test-strip-receiving module; and
   c1) the processor is programmed to:
   concurrently cause the switching unit to connect through the dummy load, cause the excitation source to provide a DC signal, and record first respective value(s) of the demodulated signal(s);
   determine a bias of the demodulator using the first respective value(s) and store the determined bias in the memory block;
   concurrently cause the switching unit to connect through the dummy load, cause the excitation source to simultaneously provide both an AC signal and the DC signal, and record second respective value(s) of the demodulated signal(s);
   determine the dummy magnitude correction and the dummy phase correction using the respective second value(s) and the determined bias of the demodulator, and store the determined dummy magnitude correction and dummy phase correction in the memory block;
   detect the insertion of a test strip in the test-strip-receiving module;
   concurrently cause the switching unit to connect through the first and second electrical pins, cause the excitation source to simultaneously provide both an AC signal and a DC signal, and after the insertion, record third respective value(s) of the demodulated signal(s); and
   determine phase and gain modifiers of the portable analytical test meter with test strip using the third respective value(s), the determined dummy magnitude correction and the determined dummy phase correction, and the determined bias of the demodulator, and store the determined phase and gain modifiers of the portable analytical test meter with test strip in the memory block.

2. The portable analytical test meter according to claim 1, wherein the processor is further programmed to:
  apply a selected electrical signal across the first and second electrical connector pins after the test strip is detected, and concurrently record fourth respective value(s) of the demodulated signal(s);
  determine one or more corrected value(s) corresponding to the fourth respective value(s) using the determined phase and gain modifiers of the portable analytical test meter with test strip, the determined dummy magnitude correction and the determined dummy phase correction, and the determined bias of the demodulator; and
  process the corrected value(s) to detect presence of a fluid sample and, if the fluid sample is present, determine the analyte.

3. The portable analytical test meter according to claim 1, wherein the processor is further programmed to:
  detect the insertion of a second test strip in the test-strip-receiving module;
  apply a selected electrical signal across the first and second electrical connector pins after the second test strip is detected, and concurrently record fourth respective value(s) of the demodulated signal(s);
  determine one or more corrected value(s) corresponding to the fourth respective value(s) using the stored determined phase and gain modifiers of the portable analytical test meter with test strip, the stored determined dummy magnitude correction, the stored determined dummy phase correction, and the stored determined bias of the demodulator; and
  process the corrected value(s) to detect presence of a fluid sample on the second test strip and, if the fluid sample is present, determine the analyte.

4. The portable analytical test meter according to claim 1, wherein:
  a) the demodulated signal(s) include a real-component signal and an imaginary-component signal;
  b) the determined bias includes a real bias component and an imaginary bias component corresponding respectively to the real-component signal and the imaginary-component signal; and
  c) the processor is programmed to additively combine the real bias component and the imaginary bias component with real component(s) and imaginary component(s), respectively, of the second, third, and fourth respective value(s).

5. The portable analytical test meter according to claim 4, wherein the excitation unit provides a first AC signal, the portable analytical test meter further comprising a phase delay unit that provides a lagged signal 90° in phase behind the first AC signal, and wherein the demodulator further includes two mixer units controlled by the first AC signal, or a signal in phase therewith, and the lagged signal, respectively, the mixer units being operative to provide the real-component signal and the imaginary-component signal, respectively.

6. The portable analytical test meter according to claim 1, wherein the switching unit includes two double-throw switches, one said switch connecting the excitation source to one of a first terminal of the dummy load and the first electrical connector pin of the test-strip-receiving module, and the other said switch connecting an input of the demodulator to one of a second terminal of the dummy load and the second electrical connector pin of the test-strip-receiving module.

7. The portable analytical test meter according to claim 1, wherein the excitation source is configured to provide voltage signals, the demodulator further comprising a transimpedance amplifier to measure current(s) and provide corresponding voltage(s), and the demodulator being adapted to provide the demodulated signal(s) using the voltage(s).

8. The portable analytical test meter according to claim 1, wherein the dummy load calibration block includes a resistor.

9. The portable analytical test meter according to claim 8, wherein the resistor is a 22KΩ precision resistor.

10. A method for calibrating a portable analytical test meter for use with an analytical test strip, the method comprising:
  determining a dummy magnitude correction and a dummy phase correction of the portable analytical test meter using a dummy load calibration circuit block of the portable analytical test meter;
  storing the dummy magnitude correction and the dummy phase correction in a memory block of the portable analytical test meter; and
  determining an analyte using the stored dummy magnitude correction and stored dummy phase correction,
  wherein the step of determining corrections includes:
  receiving an analytical test strip inserted into a test-strip-receiving module of the test meter so that first and second electrical contact pads exposed on the analytical test strip electrically contact first and second electrical connector pins of the test-strip-receiving module, respectively, the analytical test strip including a sample-receiving chamber adapted to receive a fluid sample and electrically connected between the first and second electrical contact pads;
  using an electronics module of the test meter, applying a DC signal through a dummy load to a demodulator that produces demodulated signal(s), and concurrently recording first respective value(s) of the demodulated signal(s);
  using a processor of the test meter, automatically determining a bias of the demodulator using the first respective value(s);
  using the electronics module, simultaneously applying a DC signal and an AC signal through the dummy load to the demodulator, and concurrently recording second respective value(s) of the demodulated signal(s);
  using the processor, automatically determining the dummy phase correction and the dummy magnitude correction using the respective second value(s) and the determined bias of the demodulator; and
  the step of determining the analyte includes:
  after said receiving step and using the electronics module, simultaneously applying the DC signal and an AC signal through the first and second electrical pins to the demodulator, and concurrently recording third respective value(s) of the demodulated signal(s) as measured through the electrical pins;
  using the processor, automatically determining phase and gain modifiers of the portable analytical test meter with test strip using the third respective value(s), the determined dummy phase correction and the determined dummy magnitude correction, and the determined bias of the demodulator;
  using the processor, applying a selected electrical signal across the first and second electrical connector pins after the test strip is received and concurrently measuring fourth respective value(s) of the demodulated signal(s);

using the processor, automatically determining one or more corrected value(s) corresponding to the fourth respective value(s) using the determined phase and gain modifiers of the portable analytical test meter with test strip, the determined dummy phase correction and the determined dummy magnitude correction, and the determined bias of the demodulator; and the processor automatically processing the corrected value(s) to determine the analyte in the applied fluid sample.

11. The method according to claim 10, further including automatically detecting the insertion of the analytical test strip and, in response to the detection, applying the selected electrical signal.

12. The method according to claim 11, further including automatically processing the corrected value(s) to detect whether the fluid sample applied to the test strip has filled the sample-receiving chamber.

13. The method according to claim 10, wherein the demodulated signal(s) include a real-component signal and an imaginary-component signal.

14. The method according to claim 10, wherein the bias determining step includes storing the recorded first value corresponding to the real-component signal as a first bias value and the recorded first value corresponding to the imaginary-component signal as a second bias value, so that the determined bias of the demodulator includes the first bias value and the second bias value.

15. The method according to claim 14, wherein each of the step of determining the phase and gain modifiers of the portable analytical test meter with test strip and the step of determining the dummy phase correction and the dummy magnitude correction includes additively combining the first bias value and the second bias value with the recorded respective value(s).

16. The method according to claim 10, wherein the step of measuring through the first and second electrical pins includes automatically operating a switching unit to direct the DC signal and the AC signal to the first electrical pin and to connect the second electrical pin to an input of the demodulator.

17. The method according to claim 10, wherein the selected electrical signal includes the DC signal and the AC signal applied in the step of measuring through the first and second electrical pins.

* * * * *